United States Patent
Stenzel et al.

(10) Patent No.: US 6,297,236 B1
(45) Date of Patent: Oct. 2, 2001

(54) FUNGICIDE ACTIVE SUBSTANCE COMBINATIONS

(75) Inventors: Klaus Stenzel, Düsseldorf; Stefan Dutzmann, Langenfeld; Astrid Mauler-Machnik, Leichlingen; Lutz Assmann, St. Peter-Ording, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/402,908

(22) PCT Filed: Apr. 6, 1998

(86) PCT No.: PCT/EP98/01987

§ 371 Date: Oct. 13, 1999

§ 102(e) Date: Oct. 13, 1999

(87) PCT Pub. No.: WO98/47370

PCT Pub. Date: Oct. 29, 1998

(51) Int. Cl.⁷ .......................... A61K 31/535; A01N 43/80
(52) U.S. Cl. .......................... 514/229.2; 514/380
(58) Field of Search .................. 514/380, 229.2

(56) References Cited

U.S. PATENT DOCUMENTS

| | | | |
|---|---|---|---|
| 3,912,752 | 10/1975 | Meiser et al. | 260/308 R |
| 3,952,002 | 4/1976 | Kramer et al. | 260/308 R |
| 4,048,318 | 9/1977 | Meiser et al. | 424/269 |
| 4,115,060 | 9/1978 | Finley et al. | 8/111 |
| 4,138,568 | 2/1979 | Hari et al. | 548/305 |
| 4,147,791 | 4/1979 | Meiser et al. | 424/269 |
| 4,532,341 | 7/1985 | Holmwood et al. | 549/559 |
| 4,560,693 | 12/1985 | Rainer | 514/338 |
| 4,626,595 | 12/1986 | Holmwood et al. | 549/559 |
| 4,723,984 | 2/1988 | Holmwood et al. | 71/76 |
| 4,789,672 | 12/1988 | Holmwood et al. | 514/184 |
| 4,851,405 | 7/1989 | Kramer et al. | 514/212 |
| 4,871,390 | 10/1989 | Holmwood et al. | 71/92 |
| 4,897,107 | 1/1990 | Holmwood et al. | 71/92 |
| 4,904,298 | 2/1990 | Holmwood et al. | 71/92 |
| 4,910,200 | 3/1990 | Curtze et al. | 514/237.5 |
| 4,911,746 | 3/1990 | Holmwood et al. | 71/92 |
| 4,931,560 | 6/1990 | Hubele | 544/315 |
| 4,931,581 | 6/1990 | Schurter et al. | 560/18 |
| 4,987,234 | 1/1991 | Fischer | 548/305 |
| 4,988,734 | 1/1991 | Kraatz et al. | 514/624 |
| 4,992,438 | 2/1991 | Ito et al. | 514/275 |
| 5,003,079 | 3/1991 | Meier et al. | 548/486 |
| 5,059,623 | 10/1991 | Kruger et al. | 514/613 |
| 5,145,856 | 9/1992 | Clough et al. | 514/274 |
| 5,153,200 | 10/1992 | Hubele | 514/275 |
| 5,190,928 | 3/1993 | Schurter et al. | 514/63 |
| 5,248,687 | 9/1993 | Hayase et al. | 514/346 |
| 5,264,440 | 11/1993 | Clough et al. | 514/269 |
| 5,304,572 | 4/1994 | Michelotti et al. | 514/514 |
| 5,334,607 | 8/1994 | Sauter et al. | 514/378 |
| 5,376,657 | 12/1994 | Hubele et al. | 514/253 |
| 5,453,531 | 9/1995 | Seitz et al. | 560/29 |
| 5,468,747 | 11/1995 | Clough et al. | 514/239.5 |
| 5,523,311 | 6/1996 | Schurter et al. | 548/361 |
| 5,789,430 | 8/1998 | Jautelat et al. | 514/272.4 |
| 5,859,039 | 1/1999 | Jautelat et al. | 514/384 |
| 6,020,354 | 2/2000 | Assmann et al. | 514/380 |

FOREIGN PATENT DOCUMENTS

| | | |
|---|---|---|
| 196 02 095 | 7/1997 | (DE) . |
| 754694 | 1/1997 | (EP) . |
| 517476 | 10/1997 | (EP) . |
| 2-233602 | 9/1990 | (JP) . |
| 94/04509 | 3/1994 | (WO) . |
| 94/22844 | 10/1994 | (WO) . |
| 97/06171 | 2/1997 | (WO) . |

OTHER PUBLICATIONS

Weeds, S.R. Colby, 15 (month unavailable) 1967, pp. 20–22, Calculating Synergistic & Antagonistic Responses of Herbicide Combinations.

Pesticide Manual, 9th edition, (month unavailable) 1991, pp. 206–207, 249, 431–432, 461–462, 491, 529–530, 531–532, 554–555, 654, 726, 827 and 866–867.

Primary Examiner—Allen J. Robinson
(74) Attorney, Agent, or Firm—Joseph C. Gil

(57) ABSTRACT

The novel active compound combinations consisting of a halogeno-benzimidazole of the formula

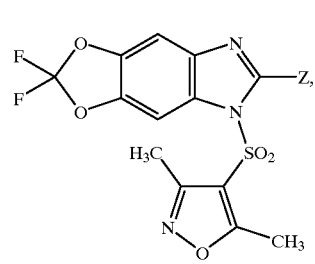

(I)

in which
Z represents chlorine or bromine,
and the active compound groups (1) to (25) listed in the description have very good fungicidal properties.

4 Claims, No Drawings

FUNGICIDE ACTIVE SUBSTANCE COMBINATIONS

This application is a 371 of PCT/EP98/01987, filed Apr. 6, 1998.

The present invention relates to novel active compound combinations which comprise known halogeno-benzimidazoles and further known fungicidally active compounds, and which are highly suitable for controlling phytopathogenic fungi.

It is already known that 1-(3,5-dimethyl-soxazole4-sulphonyl)-2-bromo-6,6-difluoro-[1,3]-dioxolo-[4,5f]-benzidazole and 1-(3,5-dimethyl-isoxaole4-sulphonyl)-2-chloro-6,6-difluoro-[1,3]-dioxolo-[4,5f]-benzimidazole have fungicidal properties (cf WO 97-06171). The activity of these compounds is good; however, at low application rates it is in some cases not satisfactory.

Furthermore, it is already known that a large number of triazole derivatives, aniline derivatives, dicarboxirnides and other heterocycles can be employed for controlling fungi (cf. EP-A 0 040 345, DE-A 2 201 063, DE-A 2 324 010, Pesticide Manual, 9th Edition (1991), pages 249 and 827, EP-A 0 382 375 and EP-A 0 515 901). Likewise, the activity of these compounds is not always satisfactory at low application rates.

Finally, it is also known that 1-[(6-chloro-3-pyridinyl)-methyl]-N-nitro-2-imidazolidineimine can be used for controlling animal pests such as insects (cf. Pesticide Manual, 9th Edition (1991), page 491). However, fungicidal properties have not hitherto been described for this compound.

It has now been found that the novel active compound combinations consisting of a halogeno-benzuimdazole of the formula

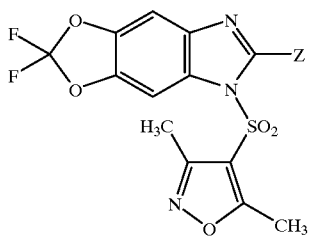

(I)

in which

Z represents chlorine or bromine, and (1) a triazole derivative of the formula

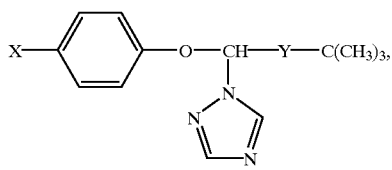

(II)

in which

X represents chlorine or phenyl, and

Y represents

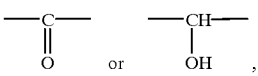

and/or (2) the triazole derivative of the formula

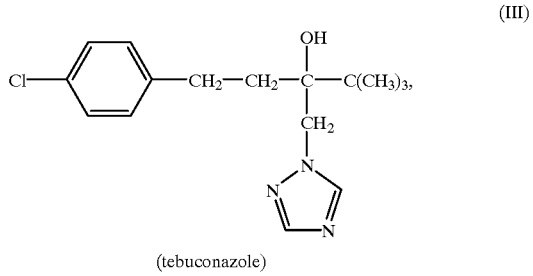

(III)

(tebuconazole)

and/or (3) an aniline derivative of the formula

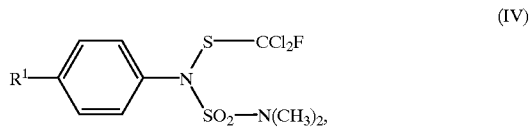

(IV)

in which $R^1$ represents hydrogen or methyl, and/or (4) N-[1-(4-chlorophenyl)-ethyl]-2,2-dichloro-1-ethyl-3-methyl-cyclopropanecarboxamide of the formula

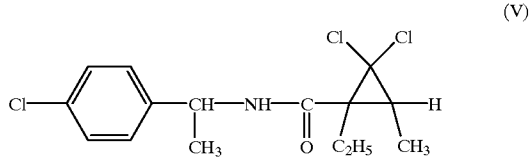

(V)

and/or (5) the zinc propylene-1,2-bis(dithiocarbamidate) of the formula

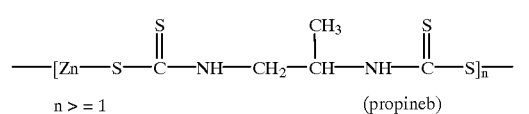

(VI)

$n \geq 1$ (propineb)

and/or (6) at least one thiocarbamate of the formula

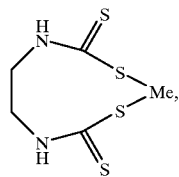
(VII)

Me=Zn or Mn or a mixture of Zn and Mn and/or (7) the aniline derivative of the formula

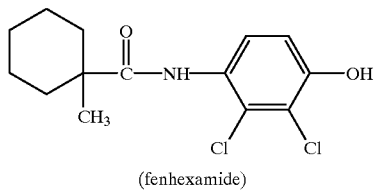
(VIII)

(fenhexamide)

and/or (8) the compound of the formula

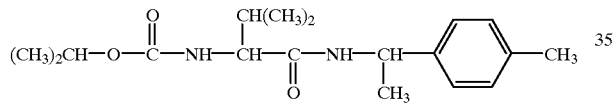
(IX)

and/or (9) the benzothiadiazole derivative of the formula

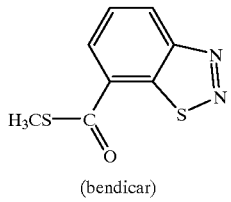
(X)

(bendicar)

and/or

(10) the 8-t-butyl-2-(N-ethyl-N-n-propyl-amino)-methyl-1,4-dioxaspiro[5,4]-decane of the formula

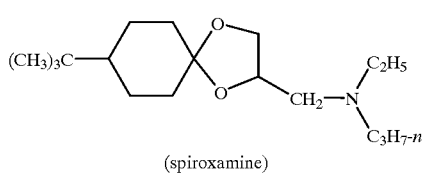
(XI)

(spiroxamine)

and/or

(11) the compound of the formula

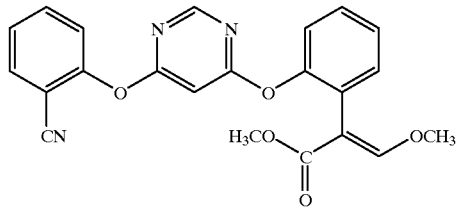
(XII)

(azoxystrobin)

and/or

(12) the compound of the formula

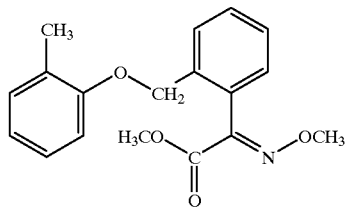
(XIII)

(kresoxim-methyl)

and/or

(13) the compound of the formula

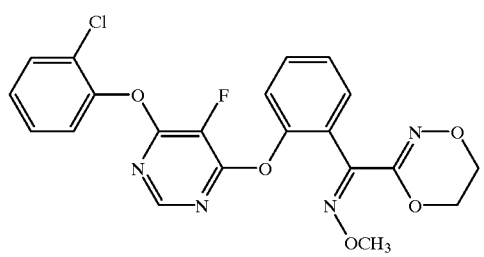
(XIV)

and/or

(14) the cyanooxime derivative of the formula

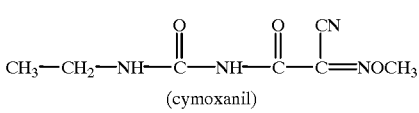
(XV)

(cymoxanil)

and/or

(15) a pyrimidine derivative of the formula

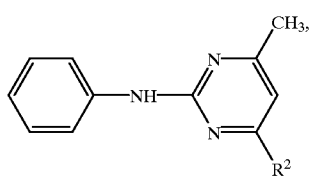 (XVI)

in which
R² represents methyl or cyclopropyl, and/or

(16) the aniline derivative of the formula

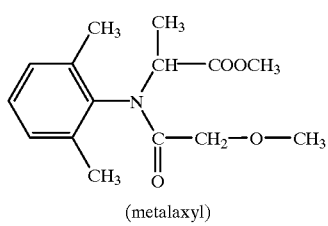 (XVII)

(metalaxyl)

and/or

(17) the morpholine derivative of the formula

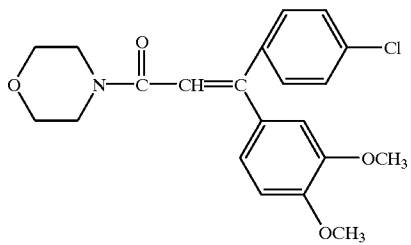 (XVIII)

(dimetomorph)

and/or

(18) the phthalimide derivative of the formula

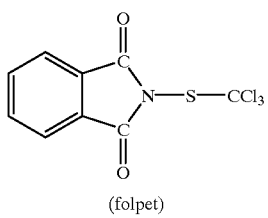 (XIX)

(folpet)

and/or

(19) the phosphorus compound of the formula

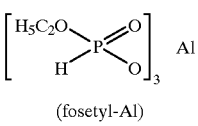 (XX)

(fosetyl-Al)

and/or

(20) the hydroxyethyl-triazole dervative of the formula

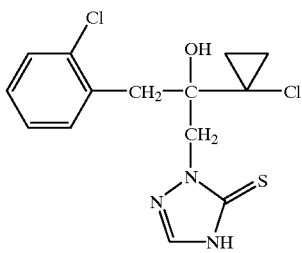 (XXI)

and/or

(21) the 1-[(6-chloro-3-pyridinyl)-methyl]-N-nitro-2-imidazolidineirnine of the formula

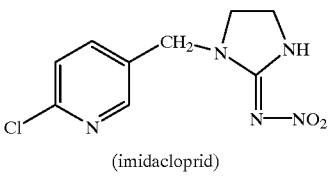 (XXII)

(imidacloprid)

and/or

(22) the oxazolidinedione of the formula

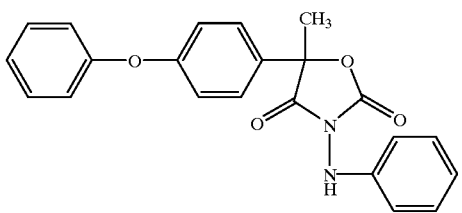 (XXIII)

(famoxadone)

and/or

(23) the benzamide derivative of the formula

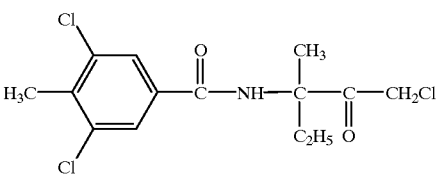 (XXIV)

and/or

(24) a guanidine derivative of the formula (XXV)

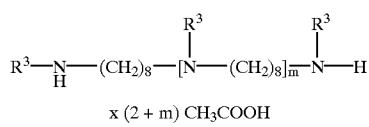

x (2 + m) CH$_3$COOH in which
m represents integers from 0 to 5 and
R$^3$ represents hydrogen (7 to 23%) or the radical of the formula

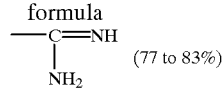

(77 to 83%)

and/or

(25) the triazole derivative of the formula (XXVI)

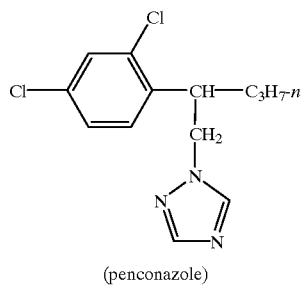

(penconazole)

have very good fungicidal properties.

Surprisingly, the fungicidal activity of the active compound combinations according to the invention is considerably higher than the sum of the activities of the individual active compounds. Thus, an unforeseeable, true synergistic effect is present, and not just an addition of activities.

The formula (I) includes
the 1-(3,5-dimethyl-isoxazole4sulphonyl)-2-bromo-6,6-difluoro-[1,3]-dioxolo-[4,5f]-benzimidazole of the formula (Ia)

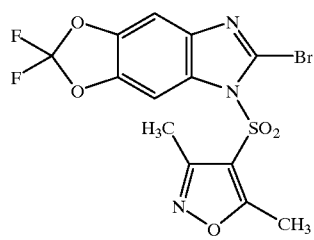

and
the 1-(3,5-dimethyl-isoxazole-4-sulphonyl)-2-chloro-6,6-difluoro-[1,3]-dioxolo-[4,5f]-benzimnidazole of the formula (Ib)

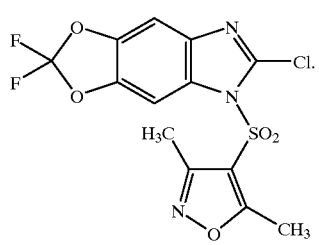

The halogeno-benzimidazoles of the formulae (Ia) and (Ib) are known (cf WO 97-06171).

The formula (II) includes the compounds
1-(4-chloro-phenoxy)-3,3-dimethyl-1-(1,2,4-triazol-1-yl)-butan-2-one of the formula (IIa)

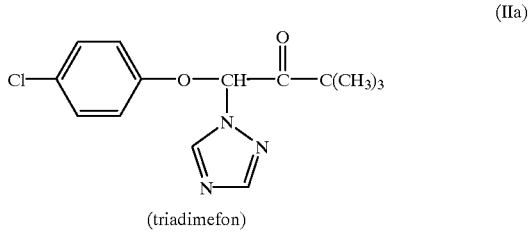

(triadimefon)

1-(4-chloro-phenoxy)-3,3-dimethyl-1-(1,2,4-triazol-1-yl)-butan-2-ole of the formula (IIb)

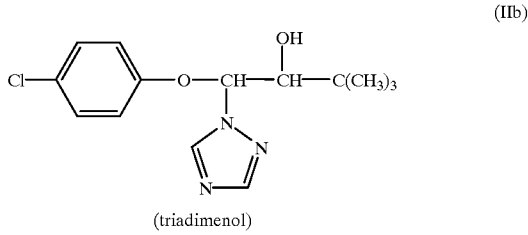

(triadimenol)

and
1-(4-phenyl-phenoxy)-3,3-dimethyl-1-(1,2,4-triazol-1-yl)-butan-2-ole of the formula (IIc)

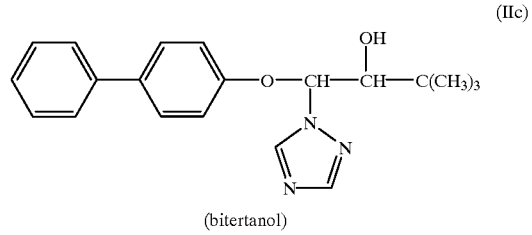

(bitertanol)

The formula (IV) includes the aniline derivatives of the formulae (IVa)

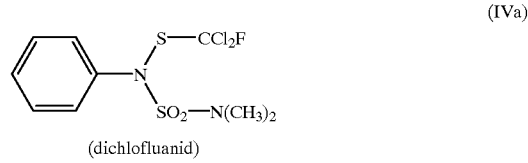

(dichlofluanid)

and (IVb)

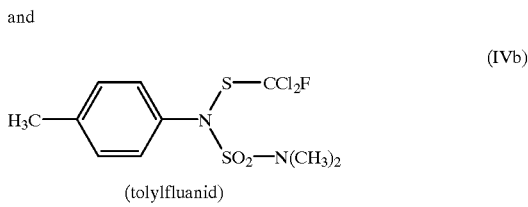

(tolylfluanid)

and
It is evident from the formula for the active compound of the formula (V) that the compound has three asymmetrically substituted carbon atoms. The product may therefore be present as a mixture of various isomers, or else in the form of a single component. Particular preference is given to the compounds N-(R)-[1-(4-chloro-phenyl)-ethyl]-(1S)-2,2-dichloro-1-ethyl-3t-methyl-1r-cyclo-propanecarboxamide of the formula

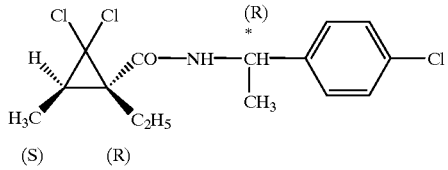

(Va)

and

N-(R)-[1-(4-chloro-phenyl)-ethyl]-(1R)-2,2-dichloro-1-ethyl-3t-methyl-1r-cyclo-propanecarboxamide of the formula

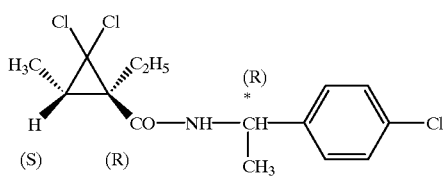

(Vb)

The formula (VII) includes the compounds

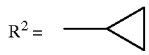

Me = Zn  (zineb)   (VIIa)

Me = Mn  (maneb) and   (VIIb)

mixture of (VIIa) and (VIIb) (mancozeb).   (VIIc)

The formula (XVI) includes the compounds

R2 = CH3  (pyrimethanil) and   (XVIa)

R² = ◁  (cyprodinyl)   (XVIb)

The hydroxyethyl-triazole derivative of the formula (XXI) can be present in the "thiono" form of the formula

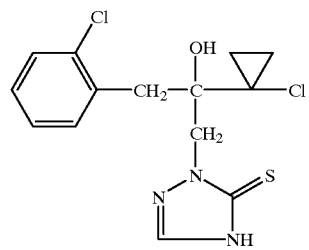

(XXI)

or in the tautomeric "mercapto" form of the formula

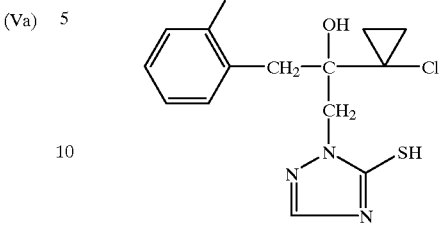

(XXIb)

For the sake of simplicity, only the "thiono" form is given in each case.

The guanidine derivative of the formula (XXV) is a substance mixture of the common name guazatine.

The components which are present in the active compound combinations according to the invention in addition to a halogeno-benzimidazole of the formula (I) are also known. Specifically, the active compounds are described in the following publications:

(1) Compounds of the formula (II)
   DE-A2201 063
   DE-A 2 324 010
(2) Compound of the formula (III)
   EP-A 0 040 345
(3) Compounds of the formula (IV)
   Pesticide Manual, 9th Edition (1991), pages 249 and 827
(4) Compound of the formula (V) and individual derivatives thereof
   EP-A 0 341 475
(5) Compound of the formula (VI)
   Pesticide Manual, 9th Edition (1991), page 726
(6) Compounds of the formula (VII)
   Pesticide Manual, 9th Edition (1991), pages 529, 531 and 866
(7) Compound of the formula (VII)
   EP-A 0 339 418
(8) Compound of the formula (IX)
   EP-A 0 472 996
(9) Compound of the formula (X)
   EP-A 0 313 512
(10) Compound of the formula (XI)
   EP-A 0281 842
(11) Compound of the formula (XII)
   EP-A 0 382 375
(12) Compound of the formula (XIII)
   EP-A03515901
(13) Compound of the formula (XIV)
   DE-A 196 02 095
(14) Compound of the formula (XV)
   Pesticide Manual, 9th edition (1991), page 206
(15) Compounds of the formula (XVI)
   EP-A 0270 111
   EP-A 0310 550
(16) Compound of the formula (XVI)
   Pesticide Manual, 9th Edition (1991), page 554
(17) Compound of the formula (XVIII)
   EP-A 0 219 756
(18) Compound of the formula (XIX)
   Pesticide Manual, 9th Edition (1991), page 431

(19) Compound of the formula (XX)
   Pesticide Manual, 9h Edition (1991), page 443
(20) Compound of the formula (XXI)
   WO 96-16048
(21) Compound of the formula (XXII)
   Pesticide Manual, 9th Edition (1991), page 491
(22) Compound of the formula (XXIII)
   EP-A 0393 911
(23) Compound of the formula (XXIV)
   EP-A 0 600 629
(24) Substance of the formula (XXV)
   Pesticide Manual, 9th Edition (1991), page 461
(25) Compound of the formula (XXVI)
   Pesticide Manual, 9th Edition (1991), page 654

In addition to an active compound of the formula (I), the active compound combinations according to the invention comprise at least one active compound of the compounds of groups (I) to (25). Additionally, they may comprise furtherer fungicidally active components.

The synergistic effect is particularly pronounced when the active compounds in the active compound combinations according to the invention are present in certain weight ratios. However, the weight ratios of the active compounds in the active compound combinations can be varied within a relatively wide range. In general, 0.1 to 20 parts by weight, preferably 0.2 to 10 parts by weight, of active compound of group (1), 0.1 to 20 parts by weight, preferably 0.2 to 10 parts by weight, of active compound of group (2), 1 to 150 parts by weight, preferably 1 to 100 parts by weight, of active compound of group (3), 0.11 to 1 parts by weight, preferably 0.2 to 5 parts by weight, of active compound of group (4), 1 to 150 parts by weight, preferably 5 to 100 parts by weight, of active compound of group (5), 1 to 150 parts by weight, preferably 5 to 100 parts by weight, of active compound of group (6), 0.1 to 50 parts by weight, preferably 1 to 20 parts by weight, of active compound of group (7), 0.11 to 50 parts by weight, preferably 0.2 to 20 parts by weight, of active compound of group (8), 0.02 to 50 parts by weight, preferably 0.1 to 10 parts by weight, of active compound of group (9), 0.1 to 20 parts by weight, preferably 0.5 to 10 parts by weight, of active compound of group (10), 0.1 to 50 parts by weight, preferably 0.2 to 20 parts by weight, of active compound of group (11), 0.1 to 50 parts by weight, preferably 0.2 to 20 parts by weight, of active compound of group (12), 0.1 to 50 parts by weight, preferably 0.2 to 20 parts by weight, of active compound of group (13), 0.1 to 50 parts by weight, preferably 0.2 to 20 parts by weight, of active compound of group (14), 0.2 to 50 parts by weight, preferably 1 to 20 parts by weight, of active compound of group (15), 0.1 to 50 parts by weight, preferably 0.2 to 20 parts by weight, of active compound of group (16), 0.1 to 50 parts by weight, preferably 0.2 to 20 parts by weight, of active compound of group (17), 1 to 150 parts by weight preferably 5 to 100 parts by weight, of active compound of group (18), 0.1 to 150 parts by weight, preferably 1 to 100 parts by weight, of active compound of group (19), 0.02 to 50 parts by weight, preferably 0.2 to 10 parts by weight, of active compound of group (20), 0.05 to 20 parts by weight, preferably 0.1 to 10 parts by weight, of active compound of group (21), 0.1 to 50 parts by weight, preferably 0.2 to 20 parts by weight, of active compound of group (22), 0.1 to 50 parts by weight, preferably 0.2 to 20 parts by weight, of active compound of group (23), 0.02 to 50 parts by weight, preferably 0.04 to 10 parts by weight, of active compound of group (24) and/or 0.2 to 50 parts by weight, preferably 1 to 20 parts by weight, of active compound of group (25), are employed per part by weight of active compound of the formula (I).

The active compound combinations according to the invention have very good fungicidal properties and can be employed for controlling phytopathogenic fungi, such as Plasmodiophoromycetes, Oomycetes, Chytridiomycetes, Zygomycetes, Ascomycetes, Basidiomycetes, Deuteromycetes, etc.

The active compound combinations according to the invention are particularly suitable for controlling cereal diseases, such as Erysiphe, Puccinia and Fusarium, and for controlling diseases encountered in viticulture, such as Uncinula, Plasmopara and Botrytis, and furthermore in dicotyledonous crops for controlling powdery and downy mildew fungi and causative organisms of leaf spot.

The fact that the active compound combinations are well tolerated by plants at the concentrations required for controlling plant diseases permits the treatment of above-ground parts of plants, of propagation stock and seeds, and of the soil. The active compound combinations according to the invention can be employed for foliar application or else as seed dressings.

The active compound combinations according to the invention can be converted to the customary formulations, such as solutions, emulsions, suspensions, powders, foams, pastes, granules, aerosols and microencapsulations in polymeric substances and in coating compositions for seeds, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulphoxide, or else water. Liquefied gaseous extenders or carriers are to be understood as meaning liquids which are gaseous at ambient temperature and under atmospheric pressure, for example aerosol propellants such as butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates, or else protein hydrolysates. Suitable dispersants are: for example ligninsulphite waste liquors and methylcellulose.

Tackifiers such as carboxymethylcellulose and natural and synthetic polymers in the form of powders, granules or lattices, such as gum arabic, polyvinyl alcohol and polyvinyl acetate, or else natural phospholipids such as cephalins and lecithins, and synthetic phospholipids can be used in the formulations. Other additives can be mineral and vegetable oils.

It is possible to use colourants such as inorganic pigment s, for example iron oxide, titanium oxide and prussian blue, and organic dyestuffs such as alizarin dyestuffs, azo dyestuffs and metal phthaloane dyestuffs, and trace nutrients such as salts of iron, manganese, boron, copper, cobalt, molybdenum and zinc.

The formulations generally comprise between 0.1 and 95% by weight of active compounds, preferably between 0.5 and 90%.

In the formulations, the active compound combinations according to the invention can be present as a mixture with other known active compounds such as fungicides, insecticides, acaricides and herbicides, and as mixtures with fertilizers or plant growth regulators.

The active compound combinations can be used as such, in the form of their formulations or as the use forms prepared therefrom, such as ready-to-use solutions, emulsifiable concentrates, emulsions, suspensions, wettable powders, soluble powders and granules. They are used in the customary manner, for example by watering, spraying, atomizing, scattering, spreading, and as a powder for dry seed treatment, a solution for seed treatment, a water-soluble powder for seed treatment, a water-soluble powder for slurry treatment, or by encrusting.

When using the active compound combinations according to the invention, the application rates can be varied within a relatively wide range, depending on the kind of application. In the treatment of parts of plants, the application rates of the active compound combination are generally between 0.1 and 10,000 g/ha, preferably between 10 and 1000 g/ha. In the treatment of seeds, the application rates of the active compound combination are generally between 0.001 and 50 g per kilogram of seed, preferably between 0.01 and 10 g per kilogram of seed. In the treatment of the soil, the application rates of the active compound combination are generally between 0.1 and 10,0009gha, preferably between 1 and 5000 g/ha.

The good fungicidal activity of the active compound combinations according to the invention is evident from the examples below. While the individual active compounds exhibit weaknesses with regard to the fungicidal activity, the combinations have an activity which exceeds a simple addition of activities.

A synergistic effect of fungicides is always present when the fungicidal activity of the active compound combinations exceeds the total of the activities of the active compounds when applied individually.

The expected activity for a given combination of two active compounds can be calculated as follows (cf. Colby, S. R, "Calculating Synergistic and Antagonistic Responses of Herbicide Combinations", Weeds 5 (1967), 20–22)

If

X is the efficacy when applying active compound A at an application rate of mg/ha, Y is the efficacy when applying active compound B at an application rate of ng/ha, and E is the efficacy when applying the active compounds A and B at application rates of m and n g/ha, then $$E = X + Y - \frac{X \cdot Y}{100}$$

The efficacy is calculated in %. 0% is an efficacy which corresponds to that of the control, while an efficacy of 100% means that no infection is observed.

If the actual fungicidal activity exceeds the calculated value, then the activity of the combination is superadditive, i.e. a synergistic effect exists. In this case, the efficacy which was actually observed must be greater than the value for the expected efficacy (E) calculated from the abovementioned formula.

The examples that follow illustrate the invention.

EXAMPLE 1

Phytophthora Test (tomato)/Protective

Solvent: 47 parts by weight of acetone

Emulsifier: 3 parts by weight of allylaryl polyglycol ether

To produce a suitable preparation of active compound, 1 part by weight of active compound or active compound combination is mixed with the stated amounts of solvent and emulsifier and the concentrate is diluted with water to the desired concentration, or a commercial formulation of active compound or active compound combination is diluted with water to the desired concentration.

To test for protective activity, young plants are sprayed with the active compound preparation at the stated application rate. After the spray coating has dried on, the plants are inoculated with an aqueous spore suspension of Phytophthora infestans. The plants are then placed in an incubation cabinet at about 20° C. and 100% relative atmospheric humidity.

Evaluation is carried out 3 days after the inoculation. 0% means an efficacy which corresponds to that of the control, while an efficacy of 100% means that no infection is observed.

Active compounds, application rates and test results are shown in the table below.

TABLE 1
*Phytophthora test (tomato)/protective*
| Active compound | Active compound application rate in g/ha | Efficacy in % |
|---|---|---|
| Known: | | |
| 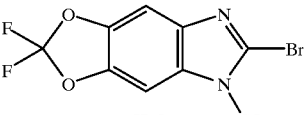 (Ia) | 1<br>0.2 | 65<br>14 |
| 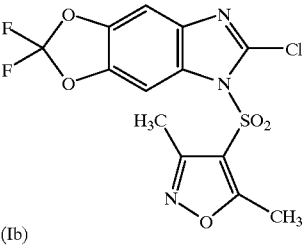 (Ib) | 1<br>0.2 | 76<br>37 |
| 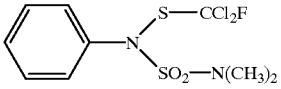 (IVa) | 2 | 0 |
| 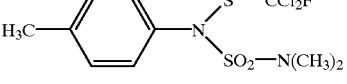 (IVb) | 2 | 26 |
| 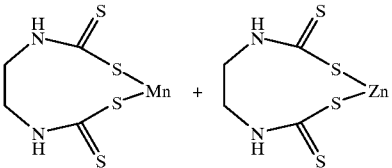 (VIIc) | 2 | 17 |
| 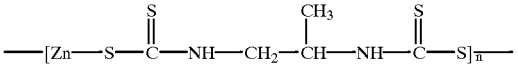 (VI) | 2 | 58 |
| 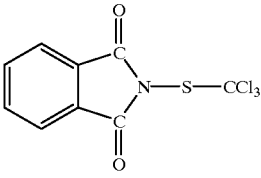 (XIX) | 2 | 12 |

TABLE 1-continued
Phytophthora test (tomato)/protective
| Active compound | Active compound application rate in g/ha | Efficacy in % |
|---|---|---|
| 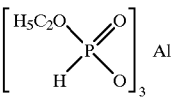 (XX) | 2 | 36 |
| 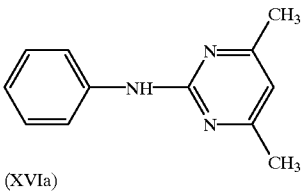 (XVIa) | 1 | 0 |
| 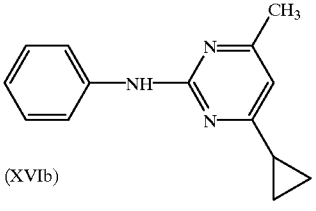 (XVIb) | 1 | 0 |
| 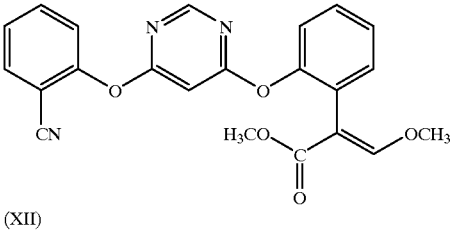 (XII) | 0.2 | 51 |
| 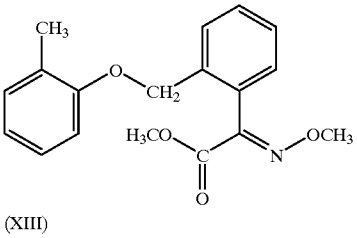 (XIII) | 0.2 | 0 |
| 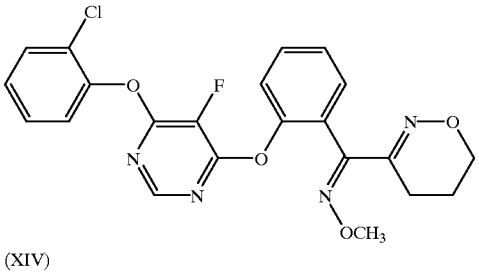 (XIV) | 1 | 27 |

TABLE 1-continued
Phytophthora test (tomato)/protective
| Active compound | Active compound application rate in g/ha | Efficacy in % |
|---|---|---|
| 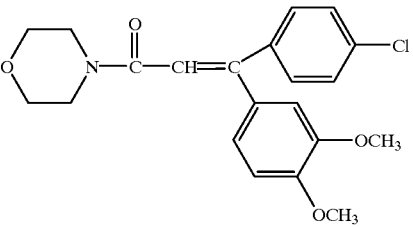<br>(XVIII) | 0.2 | 0 |
| 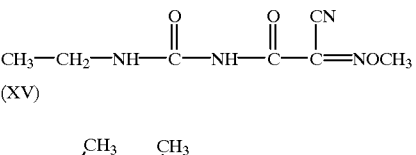<br>(XV) | 0.2 | 0 |
| 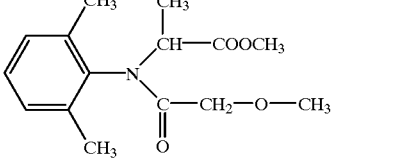<br>(XVII) | 0.2 | 0 |
| 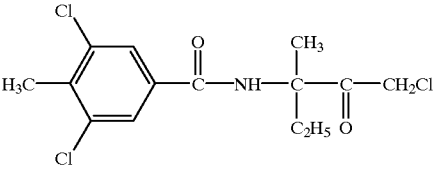<br>(XXIV) | 0.2 | 0 |
| 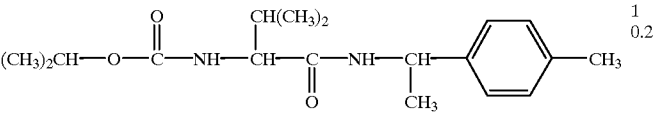<br>(IX) | 1<br>0.2 | 0<br>0 |
| 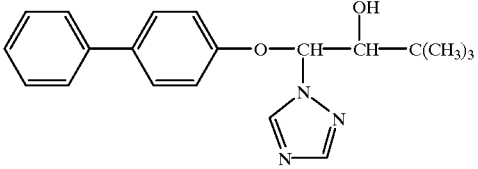<br>(IIc) | 0.2 | 24 |
| 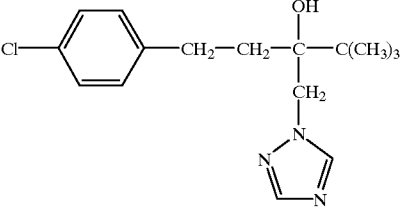<br>(III) | 0.2 | 0 |

TABLE 1-continued

Phytophthora test (tomato)/protective

| Active compound | Active compound application rate in g/ha | Efficacy in % |
|---|---|---|
| (IIa) 4-Cl-C6H4-O-CH(triazolyl)-C(=O)-C(CH3)3 | 0.2 | 0 |
| (IIb) 4-Cl-C6H4-O-CH(triazolyl)-CH(OH)-C(CH3)3 | 0.2 | 0 |
| (XXI) 2-Cl-C6H4-CH2-C(OH)(CH2-triazolyl-thione)-C(cyclopropyl)(Cl) | 0.2 | 0 |
| (XI) (CH3)3C-cyclohexyl-dioxolane-CH2-N(C2H5)(C3H7-n) | 0.2 | 5 |
| (VIII) 1-methylcyclohexyl-C(=O)-NH-(2,3-dichloro-4-hydroxyphenyl) | 5 | 0 |

TABLE 1-continued
Phytophthora test (tomato)/protective
| Active compound | Active compound application rate in g/ha | Efficacy in % |
|---|---|---|
| 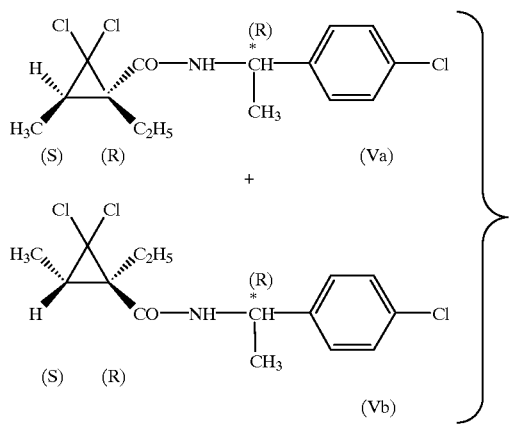 (Va) + (Vb) (1:1-mixture) | 1 | 0 |
| 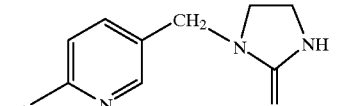 (XXII) | 0.2 | 6 |
| According to the invention: | | found calc.*) |
| (Ia) + (IVa) (1:10) 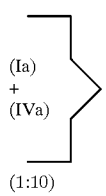 | 0.2 + 2 | 54   14 |
| (Ib) + (IVa) (1:10) 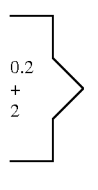 | 0.2 + 2 | 55   37 |
| (Ia) + (IVb) (1:10) 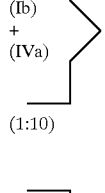 | 0.2 + 2 | 74   36 |

TABLE 1-continued

Phytophthora test (tomato)/protective

| Active compound | Active compound application rate in g/ha | Efficacy in % |
|---|---|---|
| (Ib) + (IVb) (1:10) | 0.2 + 2 | 86 53 |
| (Ia) + (VIIc) (1:10) | 0.2 + 2 | 73 29 |
| (Ib) + (VIIc) (1:10) | 0.2 + 2 | 70 48 |
| (Ia) + (VI) (1:10) | 0.2 + 2 | 79 64 |
| (Ib) + (VI) (1:10) | 0.2 + 2 | 93 74 |
| (Ib) + (XIX) (1:10) | 0.2 + 2 | 71 45 |
| (Ib) + (XX) (1:10) | 0.2 + 2 | 83 60 |

TABLE 1-continued

Phytophthora test (tomato)/protective

| Active compound | Active compound application rate in g/ha | Efficacy in % | |
|---|---|---|---|
| (Ib) + (XVIa) (1:5) | 0.2 + 1 | 69 | 37 |
| (Ib) + (XVIb) (1:5) | 0.2 + 1 | 81 | 37 |
| (Ib) + (XII) (1:1) | 0.2 + 0.2 | 87 | 69 |
| (Ia) + (XIII) (1:1) | 0.2 + 0.2 | 71 | 14 |
| (Ib) + (XIII) (1:1) | 0.2 + 0.2 | 75 | 37 |
| (Ia) + (XIV) (1:5) | 0.2 + 1 | 73 | 37 |
| (Ib) + (XIV) (1:5) | 0.2 + 1 | 75 | 54 |

TABLE 1-continued

Phytophthora test (tomato)/protective

| Active compound | Active compound application rate in g/ha | Efficacy in % | |
|---|---|---|---|
| (Ia) + (XVIII) (1:1) | 0.2 + 0.2 | 46 | 14 |
| (Ib) + (XVIII) (1:1) | 0.2 + 0.2 | 81 | 37 |
| (Ia) + (XV) (1:1) | 0.2 + 0.2 | 56 | 14 |
| (Ib) + (XV) (1:1) | 0.2 + 0.2 | 67 | 37 |
| (Ia) + (XVII) (1:1) | 0.2 + 0.2 | 73 | 14 |
| (Ib) + (XVII) (1:1) | 0.2 + 0.2 | 58 | 37 |
| (Ib) + (XXIV) (1:1) | 0.2 + 0.2 | 50 | 37 |

TABLE 1-continued

Phytophthora test (tomato)/protective

| Active compound | Active compound application rate in g/ha | Efficacy in % |
|---|---|---|
| (Ia) + (IX) (1:1) | 1 + 1 | 82 65 |
| (Ib) + (IX) (1:1) | 0.2 + 0.2 | 67 37 |
| (Ib) + (IIc) (1:1) | 0.2 + 0.2 | 85 52 |
| (Ia) + (III) (1:1) | 0.2 + 0.2 | 51 14 |
| (Ib) + (III) (1:1) | 0.2 + 0.2 | 71 37 |
| (Ia) + (IIa) (1:1) | 0.2 + 0.2 | 56 14 |
| (Ib) + (IIa) (1:1) | 0.2 + 0.2 | 84 37 |

TABLE 1-continued

Phytophthora test (tomato)/protective

| Active compound | Active compound application rate in g/ha | Efficacy in % | |
|---|---|---|---|
| (Ia) + (IIb) (1:1) | 0.2 + 0.2 | 67 | 14 |
| (Ib) + (IIb) (1:1) | 0.2 + 0.2 | 75 | 37 |
| (Ia) + (XXI) (1:1) | 0.2 + 0.2 | 51 | 14 |
| (Ib) + (XXI) (1:1) | 0.2 + 0.2 | 69 | 37 |
| (Ia) + (XI) (1:1) | 0.2 + 0.2 | 67 | 18 |
| (Ib) + (XI) (1:1) | 0.2 + 0.2 | 87 | 40 |
| (Ia) + (VIII) (1:5) | 1 + 5 | 90 | 65 |

TABLE 1-continued

Phytophthora test (tomato)/protective

| Active compound | Active compound application rate in g/ha | Efficacy in % |
|---|---|---|
| (Ib) + (VIII) (1:5) | 1 + 5 | 90 76 |
| (Ia) + (Va/Vb) (1:1) | 1 + 1 | 89 65 |
| (Ib) + (Va/Vb) (1:1) | 1 + 1 | 95 76 |
| (Ia) + (XXII) (1:1) | 0.2 + 0.2 | 73 19 |
| (Ib) + (XXII) (1:1) | 0.2 + 0.2 | 90 41 | found = efficacy found
calc. = efficacy calculated using the Colby formula

EXAMPLE 2
Fusarium Nivale Test (triticale)/Seed Treatment

The active compounds are applied as dry seed dressings. These are prepared by extending the respective active compound or the active compound combination with ground minerals to give a finely pulverulent mixture which ensures uniform distribution on the seed surface.

To dress the seed, the infected seed together with the seed dressing is shaken for 3 minutes in a sealed glass flask.

2×100 corns of triticale are sown at a depth of 1 cm in standard soil and cultivated in a greenhouse at a temperature of about 10° C. and a relative atmospheric humidity of about 95% in seed trays which receive a light regimen of 15 hours per day.

About 3 weeks after sowing, the plants are evaluated for symptoms. 0% means an efficacy which corresponds to that of the control, while an efficacy of 100% means that no infection is observed.

Active compounds, application rates and test results are shown in the table below.

TABLE 2

Fusarium nivale test (triticale)/seed treatment

| Active compound | Active compound application rate in mg/kg of seed | Efficacy in % |
|---|---|---|
| Known: | | |
| (Ia) | 100 | 26 |
| (Ib) | 500 | 0 |
| | 100 | 0 |
| (XXII) | 100 | 0 |

TABLE 2-continued

Fusarium nivale test (triticale)/seed treatment

| Active compound | Active compound application rate in mg/kg of seed | Efficacy in % |
|---|---|---|
| (IX) | 500 | 0 |
| (VIIc) | 100 | 0 |
| (IVb) | 100 | 3 |
| Mixtures according to the invention: | | |
| (Ia + VIIc) (1:1) | 50 + 50 | 66 |
| (Ib + XXII) (1:1) | 50 + 50 | 36 |
| (Ib + IX) (1:1) | 250 + 250 | 43 |
| (Ib + VIIc) (1:1) | 50 + 50 | 32 |
| (Ib + IVb) (1:1) | 50 + 50 | 75 |

EXAMPLE 3
Pythium sp. Test (pea) 1 Seed Treatment

The active compounds are applied as dry seed dressings. These are prepared by extending the respective active compound or the active compound combination with ground minerals to give a finely pulverulent mixture which ensures uniform distribution on the seed surface.

To dress the seed, the infected seed together with the seed dressing is shaken for 3 minutes in a sealed glass flask.

21×50 corns of seed are sown at a depth of 2 cm in compost soil naturally infected with phythium sp. and cultivated in a greenhouse at a temperature of about 20° C. in seed trays which receive a light regimen of 15 hours per day.

Evaluation is carried out after 14 days. 0% means an efficacy which corresponds to that of the control, while an efficacy of 100% means that no infection is observed.

Active compounds, application rates and test results are shown in the table below.

TABLE 3

Pythium sp. test (pea)/seed treatment

| Active compound | Active compound application rate in mg/kg of seed | Efficacy in % |
|---|---|---|
| Known: | | |
| (Ia) | 500 | 1 |
| (Ib) | 1000 | 4 |
| (VIIc) | 1000 | 8 |
| (IVb) | 1000 | 42 |
|  | 500 | 37 |
| Mixtures according to the invention: | | |
| (Ia + IVb) (1:1) | 250 + 250 | 55 |
| (Ib + VIIc) (1:1) | 500 + 500 | 38 |
| (Ib + IVb) (1:1) | 500 + 500 | 59 |

What is claimed is:

1. A fungicidal composition comprising synergistic fungicidally effective amounts of an active compound combination comprising (a) a halogeno-benzimidazole of the formula:

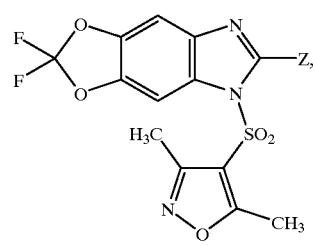

(I)

wherein Z is chlorine or bromine, (b) a compound of the formula

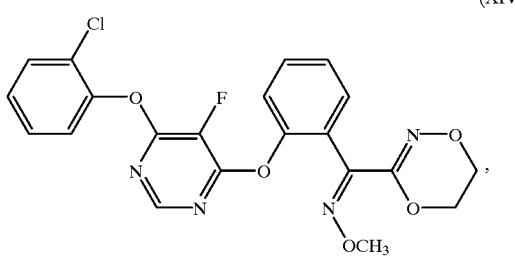

(XIV)

wherein the weight ratio of component (a) to component (b) is from 1:0.02 to 1:20.

2. The fungicidal composition of claim 1, wherein Z in formula I is chlorine.

3. The composition of claim 1 wherein the weight ratio is 1:5.

4. A method for controlling fungi comprising applying a synergistic fungicidally effective amount of an active compound combination according to claim 1 to the fungi and/or their habitat.

* * * * *